United States Patent [19]

Horimoto

[11] Patent Number: 4,547,171

[45] Date of Patent: Oct. 15, 1985

[54] STUFFED TOY

[75] Inventor: Yukihiro Horimoto, Osaka, Japan

[73] Assignee: Young Sangyo Co., Ltd., Osaka, Japan

[21] Appl. No.: 561,397

[22] Filed: Dec. 14, 1983

[30] Foreign Application Priority Data

Aug. 25, 1983 [JP] Japan .................. 58-130413[U]

[51] Int. Cl.⁴ ............................................. A63H 3/02
[52] U.S. Cl. .................................... 446/370; 446/72; 446/485
[58] Field of Search ...................... 446/72, 73, 74, 75, 446/76, 369, 370, 385, 485, 371, 372, 373; 362/124, 808

[56] References Cited

U.S. PATENT DOCUMENTS

| 1,349,374 | 8/1920 | Gruenfeld, Jr. | 362/124 |
| 2,274,303 | 2/1942 | Ornstein | 446/369 |
| 2,591,379 | 4/1952 | Schradermeier | 446/74 |
| 2,748,256 | 5/1956 | Moran | 362/808 |
| 2,932,917 | 4/1960 | Patane | 446/485 |

Primary Examiner—Robert A. Hafer
Assistant Examiner—Daniel Nolan
Attorney, Agent, or Firm—Armstrong, Nikaido, Marmelstein & Kubovcik

[57] ABSTRACT

A stuffed toy which is also useful as a bag for small articles comprising an outer stuffed fabric member having a figure or animal configuration, an inner frame assembly removably covered by said fabric member and consisting of parts detachably connected together and an illumination device mounted within said inner frame assembly. The inner frame assembly comprises a conical frame member, a cylindrical base member detachably connected at the upper edge to the lower end of the conical frame member and a bottom member detachably connected at the upper edge to the lower edge of said base member. The illumination device comprises a power source means mounted within said base member and having an upright socket receiving member, batteries mounted within said power source means, a socket received in said socket receiving member, a lamp screwed into said socket, a switch and electrical cord means electrically connecting between the components of the illumination device. The outer stuffed fabric member includes a slit and a fastener. The slit, when the fastener is open, allows the inner frame assembly to be mounted in the stuffed fabric member and to be removed therefrom to thereby convert the stuffed fabric member into a useful bag for small articles.

14 Claims, 3 Drawing Figures

STUFFED TOY

BACKGROUND OF THE INVENTION

This invention relates to a stuffed toy having a light source incorporated therein and more particularly, to a stuffed toy of the type which is also useful as a bag for small articles.

There have been proposed and practically used a variety of stuffed toys in the form of an animal or figure having a light source incorporated therein in which the eyes or face of the animal or figure are adapted to emit light. However, such prior art stuffed toys have the light source integrally formed with the stuffed fabric and thus, the conventional stuffed toys finds its exclusive utility as a light emitting toy. One example of the prior art light emitting stuffed devices is illustrated and described in Japanese Utility Model Application No. 95272/1976 filed in the name of Masao Ito on July 17, 1983 and laid open under Laid-Open Application No. 14385/1978 on Feb. 6, 1978. The light emitting stuffed device of the Japanese utility model application comprises an outer stuffed fabric having an animal configuration, a substantially conical inner light permeable light source cover or frame member over which the stuffed fabric is applied to be supported thereby, a hollow cylindrical base member connected to the lower end of the light source cover or frame member, a socket extending uprightly from the base member, a lamp screwed into the socket, a switch and an attachment plug. However, the prior art stuffed device relies upon an external power source and is used exclusively as a light emitting stuffed device. The stuffed device can only be used where an external power source is available.

Another example of the prior art light emitting stuffed devices is illustrated and described in Japanese Utility Model Application No. 8512/1972 filed in the name of Hishitomo Rubber Industry Co., Ltd. on Jan. 18, 1972 and laid open under Laid Open Application No. 84682/1973 on Oct. 15, 1973. The light emitting stuffed device of Japanese Utility Model Application No. 8512/1972 comprises a hollow base, a light source assembly mounted within the hollow base, a lamp shade or frame member extending uprightly from the hollow base, a fiber layer flocked over at least portion of the outer surface of the lamp shade by flocking process and an attachment plug electrically connected to the light source assembly. Like the above-mentioned stuffed device shown in Japanese Utility Model Application No. 9572/1976, the stuffed device of the second-mentioned Japanese utility model application also serves exclusively as a stuffed toy and can not be employed as a bag for small articles. Similarly, the stuffed device relies upon an external power source to energize the light source.

In Japanese Utility Model Application Publication No. 6148/1981 published for opposition on Feb. 10, 1981 (Japanese Utility Model Application No. 121690/1978 filed in the name of Matsushita Electric Industry Co., Ltd. on Sept. 4, 1978), there is illustrated and described an animal toy having a light source incorporated therein. The animal toy comprises an outer stuffed shell formed of synthetic resin and having ears at the top and a base at the lower end, the ears being formed with radiation holes and the base being formed with air intake ports, respectively, a support plate secured to the base, an upright socket secured to the support plate, a lamp screwed into the socket, a heat insulation plate extending through the socket and lamp and to a position above the lamp, an electrical cord extending from the socket to an external power source. In the animal toy having a light source incorporated therein as disclosed in the Japanese utility model application publication, the air heated by the energized lamp within the interior of the shell is guided along the heat insulation plate and discharges to the atmosphere through the radiation holes in the ears to prevent the shell from deforming due to the heated air. However, the animal toy is also employed exclusively as a toy and relies upon an external power source to energize the lamp.

SUMMARY OF THE INVENTION

Therefore, one object of the present invention is to provide a light emitting stuffed toy which is also useful as a bag for small articles by merely taking the inner frame assembly and illumination device out of the outer stuffed fabic without modifying the toy itself.

Another object of the present invention is to provide a stuffed toy which is also useful as a bag for small articles which comprises a relatively small number of parts and is suitable for mass production.

Another object of the present invention is to provide a stuffed toy which is also useful as a bag for small articles having the power source for energizing the lamp incorporated therein and operable even when an external power source is not available.

Another object of the present invention is to provide a stuffed toy which is also useful as a bag for small articles in which when the outer stuffed fabric becomes dirty the fabric is removed from the stuffed toy for washing whereby the service life of the toy is extended.

Another object of the present invention is to provide a stuffed toy which is also useful as a bag for small articles in which when the service life of the internal power source terminates, the power source can be easily replaced by a new power source by merely removing a part of the stuffed toy without disassembling the entire toy.

According to the present invention there has been provided a stuffed toy which is also useful as a bag for small articles which essentially comprises an outer stuffed fabric having a figure or animal configuration; an inner frame assembly detachably covered by the fabric and including a substantially conical light permeable frame member, a cylindrical base member detachably connected to the conical frame member and a dish-shaped bottom member detachably connected to the base member; and an illumination device mounted within the cylindrical member and including a power source means and a light source means.

The above and other objects and attendant advantages of the present invention will be more readily apparent to those skilled in the art from a reading of the following detailed description in conjunction with the accompanying drawings which show one preferred embodiment of the invention for illustration purpose only, but not for limiting the scope of the same in any way.

BRIEF DESCRIPTION OF THE DRAWINGS

The accompanying drawings show the preferred embodiment of the stuffed toy constructed in accordance with the principle of the present invention in which.

PREFERRED EMBODIMENT OF THE INVENTION

Figure 1:
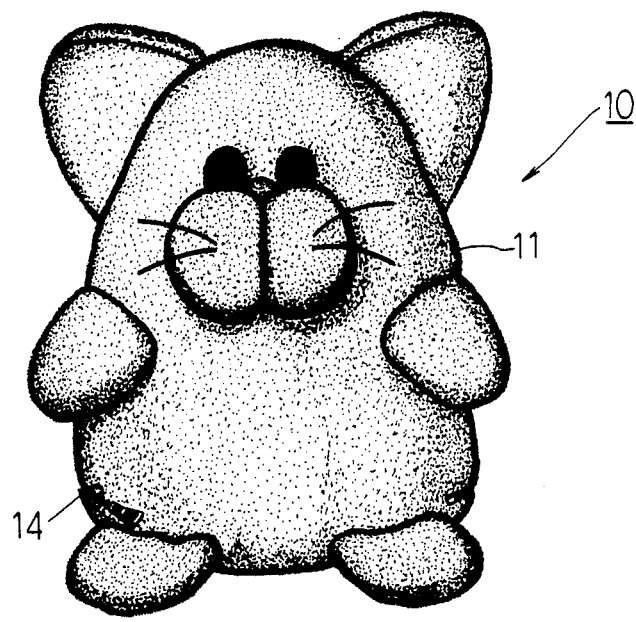
FIG. 1 is a front elevational view of the stuffed toy.
Figure 2:
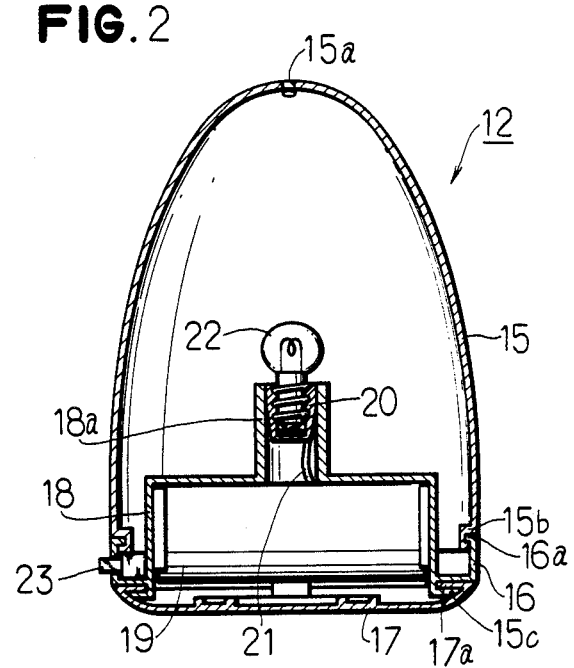
FIG. 2 is a vertically sectional view of the stuffed toy as shown in FIG. 1.
Figure 3:
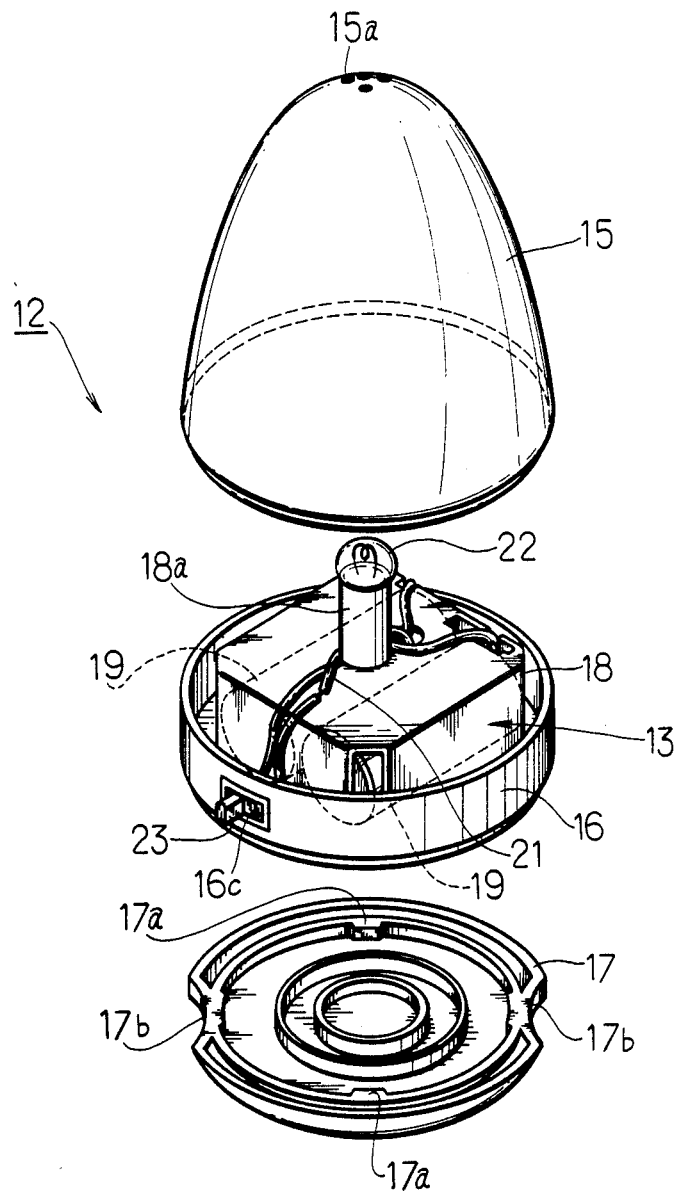
FIG. 3 is an exploded perspective view of the inner frame member of the stuffed toy as shown in FIGS. 1 and 2.

The present invention will be now described referring to the accompanying drawings in which one preferred embodiment of the stuffed toy constructed in accordance with the principle of the present invention is shown for illustration purpose only, but not for limiting the scope of the same in any way.

The stuffed toy of the invention is generally shown by reference numeral 10 and generally comprises an outer stuffed fabric 11 which is formed of Nylon or cloth and has an animal configuration in the illustrated embodiment, an inner frame assembly 12 formed of synthetic resin and detachably covered by the stuffed fabric 11 and an illumination device 13 received within the frame assembly 12. The outer stuffed fabric 11 having the animal configuration is in the form of an envelope and provided with a slit (not shown) which extends about the envelope adjacent to the lower end thereof by a distance and is normally closed by a fastener 14.

The inner frame assembly 12 comprises three parts which are detachably connected together, that is, a substantially conical light permeable frame member 15 having radiation holes 15a at its top, a cylindrical base member 16 detachably connected at the upper edge to the lower end of its frame member 15 and a dish-shaped bottom member 17 detachably connected at the upper edge to the lower edge of the base member 16. The frame member 15 is formed at the lower end thereof with diametrically opposite substantially U-shaped recesses 15b and the base member 16 is formed at the upper edge thereof with diametrically opposite inwardly extending ears 16a which engage in the associated U-shaped recesses 15b in the frame member 15 and an opening 16c in the periphery thereof for the purpose to be described hereinafter. The cylindrical base member 16 is further formed with diametrically opposite substantially L-shaped projections 15c extending downwardly from the bottom of the member 16 with the horizontal portions of the projections defining openings in cooperation with the bottom of the member 16 and the bottom member 17 is formed with inwardly extending ears 17a in diametrically opposite positions in the periphery thereof to engage in the openings defined by the projections 15c and the bottom of the base member 16. The bottom member 17 is also formed with recesses 17b in diametrically opposite positions of the periphery thereof between the projections 17b so that the bottom member 17 can be easily turned when the bottom member is connected to and disconnected from the base member 16.

The illumination device 13 comprises a box-shaped power source means 18 which opens at the bottom and has a cylindrical socket receiving member 18a extending uprightly from the top thereof, said power source means being integrally formed with and surrounded by the cylindrical base member 16, batteries 19 mounted within the power source means 18, a socket 20 fitted within the socket receiving member 18a. electrical cord means 21 electrically connected to the batteries 19, a lamp 22 screwed into the socket 20 and a power source switch 23 electrically connected to the batteries 19 by the electrical cord means 21 and projecting externally from the power source means 18 and extending through the opening 16c in the cylindrical base member 16.

With the above-mentioned construction and arrangement of the components of the stuffed toy constructed in accordance with the principle of the present invention, when the stuffed toy is employed as a toy, the fastener 14 on the outer stuffed fabric 11 is opened and the inner frame assembly 12 having the illumination device 13 connected thereto is inserted into the fabric 11. Thereafter, the fastener 14 is closed.

Since the outer stuffed fabric 11 surrounding the inner frame assembly 12 and illumination device 13 is formed of a flexible material such as Nylon or cloth, the power source switch 23 can be easily located and simply turned on and off from the exterior of the outer stuffed fabric 11. In addition, since the power source switch 23 is entirely covered by the fabric 11, the power source consists of the internal batteries 19 and no external electrical cord is employed, the toy presents the external appearance of an ordinary stuffed toy and when the power source switch 23 is turned on, the light from the lamp 22 is diffused through the light permeable frame member 15 of the inner frame assembly 12 to illuminate the entire outer stuffed fabric 11 to thereby provide a great interesting stuffed toy. In addition, since the light permeable frame member 15 of the inner frame assembly 12 is formed at the top thereof with the radiation holes 15a, there is no possibility that heat accumulates within the stuffed toy to thereby ensure safety on the part of children who play with the stuffed toy. When the batteries 19 have come to the end of their service life, the fastener 14 is opened and the bottom member 17 is disconnected from the cylindrical base member 16, the used batteries 19 are taken out of the power source means 18, new batteries 19 are positioned within the power source means 18 and the fastener 14 is closed. The battery replacement operation can be simply and easily performed without removing the inner frame assembly 12 and illumination device 13 except for the batteries 19 out of the outer stuffed fabric 11. Since the outer stuffed fabric 11 and the inner frame assembly 12 are formed as separate members, when the outer stuffed fabric 11 became dirty, the fabric can be easily removed from the inner frame assembly 12 and washed. When the inner frame assembly 12 and illumination device 13 are removed out of the outer stuffed fabric 11, the fabric 11 with the fastener sewn thereon can be employed as a bag for small articles to thereby enhance the value of commercial product with the increased versatility of the stuffed toy. Lastly, since the stuffed toy having a relatively small number of parts in simple in construction and less expensive, the stuffed toy is suitable for mass production.

Thus, the present invention has provided a stuffed toy which has an increased commercial value as a mascot toy and increased interesting effects as a decorative article and which is also useful as a bag for small articles The stuffed toy provides increased practical utility.

While only one embodiment of the present invention has been shown and described in detail, it will be understood that the same is for illustration purpose only and not to be taken as a definition of the invention, reference being had for this purpose to the appended claims.

What is claimed is:

1. A stuffed toy also useful as a bag for small articles comprising an outer stuffed fabric member having an outer figure or animal configuration and an inner frame assembly removably mounted within said stuffed fabric member for receiving a light source therein, said removable inner frame assembly having power source means mounted at the lower end of said frame assembly, said inner frame assembly comprising a substantially conical light permeable frame member, a cylindrical base member and a bottom member which are detachably connected together and an opening and closing means on said outer stuffed fabric member for mounting said inner frame assembly within and removing said inner frame assembly from said stuffed fabric member to thereby convert said stuffed toy into a bag for small articles.

2. The stuffed toy also useful as a bag for small articles as set forth in claim 1, in which said power source means is mounted within said conical frame member and comprises batteries, a switch and electric cord means electrically connecting said batteries, said switch and a light source, said light source comprises a socket supported on said power source means and a lamp screwed into said socket.

3. The stuffed toy also useful as a bag for small articles as set forth in claim 2, said conical light permeable frame member has radiation holes at the top of the frame member and said base member has an opening in the periphery of the base member through which said switch extends.

4. The stuffed toy also useful as a bag for small articles as set forth in claim 1, in which said conical frame member, said cylindrical base member and said bottom member are detachably connected together by mating engaging means.

5. The stuffed toy also useful as a bag for small articles as set forth in claim 4, in which said mating engaging means comprises diametrically opposite substantially U-shaped recesses formed in the periphery of said conical frame member at the lower end of the conical member, diametrically opposite ears extending inwardly from said cylindrical base member at the upper edge thereof to engage in said recesses, diametrically opposite substantially L-shaped projections extending downwardly from the bottom of said base member to define openings therewith and diametrically opposite ears extending inwardly from said bottom member at the upper edge thereof to engage in said openings defined by the bottom of said base member and said L-shaped projections.

6. The stuffed toy also useful as a bag for small articles as set forth in claim 5, in which said bottom member further has diametrically opposite recesses in the periphery of the bottom member.

7. The stuffed toy also useful as a bag for articles as set forth in claim 2, in which said bottom member is in the form of a dish.

8. A stuffed toy also useful as a bag for small articles, comprising an outer stuffed fabric member; an inner frame assembly removably covered by said outer stuffed fabric member and including a substantially conical light permeable frame member, a cylindrical base member detachably connected to said conical frame member and a dish-shaped bottom member detachably connected to said base member; an illumination device mounted within said cylindrical base member and including a power source means and a light source means; and an opening and closing means on said outer stuffed fabric member for placing said stuffed fabric member over said inner frame assembly for covering said frame assembly and for removing said stuffed fabric member from said frame assembly to thereby convert said stuffed toy into a bag for small articles.

9. The stuffed toy also useful as a bag for small articles as set forth in claim 8, in which said conical frame member has radiation holes at the top thereof.

10. The stuffed toy also useful as a bag for small articles as set forth in claim 8, in which said conical frame member, said cylindrical member and said bottom member are detachably connected together by mating engaging means.

11. The stuffed toy also useful as a bag for small articles as set forth in claim 10, in which said mating engaging means comprises diametrically opposite recesses formed in the periphery of said conical frame member at the lower end thereof, diametrically opposite ears extending inwardly from said cylindrical member at the upper edge thereof to engage in said recesses, diametrically opposite substantially L-shaped projections extending downwardly from said cylindrical member to define openings in cooperation with the cylindrical member and ears extending inwardly from said bottom member at the upper edge thereof to engage in said openings.

12. The stuffed toy also useful as a bag for small articles as set forth in claim 8, in which said bottom member further has diametrically opposite recesses formed in the periphery of the bottom member between said ears thereon.

13. The stuffed toy also useful as a bag for small articles as set forth in claim 8, in which said power source means comprises batteries, a switch and electrical cord means connecting between said batteries and switch and said light source means comprises a socket supported on said power source means and electrically connected to said electrical cord means and a lamp screwed into said socket.

14. The stuffed toy also useful as a bag for small articles as set forth in claim 9, in which said opening and closing means on said outer stuffed fabric member includes a slit extending by distance about said fabric member and a fastener having an open and a closed position secured to said slit, said inner frame assembly being removable from said stuffed fabric member through said slit when said fastener is in open position thereby converting said stuffed toy into a bag for small articles.

* * * * *